United States Patent [19]

Ohtawa et al.

[11] Patent Number: 5,318,727
[45] Date of Patent: Jun. 7, 1994

[54] MILD CATIONIC SURFACTANTS HAVING GOOD FOAMING CONDITIONING PROPERTIES AND CLEANING COMPOSITIONS

[75] Inventors: Yasuki Ohtawa; Makoto Kubo; Hiroyuki Imoto, all of Wakayama; Takashi Matsuo, Saitama; Kazuyuki Yahagi, Tokyo; Koshiro Sotoya, Wakayama, all of Japan

[73] Assignee: Kao Corporation, Tokyo, Japan

[21] Appl. No.: 744,942

[22] Filed: Aug. 14, 1991

[30] Foreign Application Priority Data

Aug. 23, 1990 [JP] Japan .................. 2-222194
Oct. 12, 1990 [JP] Japan .................. 2-274860

[51] Int. Cl.$^5$ ............... A61K 7/075; A61K 7/50; C07C 233/89; C11D 1/62
[52] U.S. Cl. ............... 252/547; 252/173; 252/528; 252/DIG. 5; 252/DIG. 13; 252/DIG. 14; 424/70; 554/52; 554/55; 554/66; 554/69
[58] Field of Search ............... 424/70; 252/547, 545, 252/551, DIG. 13, DIG. 5, 174.18, 174.23, 174.24, 8.75, 8.8, 548; 554/52, 55, 66, 69

[56] References Cited

U.S. PATENT DOCUMENTS

| | | | |
|---|---|---|---|
| 2,243,980 | 6/1941 | Rheiner | 252/8.8 |
| 2,340,881 | 2/1944 | Kelley | 252/8.8 |
| 3,454,494 | 7/1969 | Clark | 252/8.8 |
| 3,630,895 | 12/1971 | Krause et al. | 252/8.75 |
| 3,697,452 | 10/1972 | Olson | 252/545 |
| 3,704,228 | 11/1972 | Eckert | 252/117 |
| 3,849,348 | 11/1974 | Hewitt | 252/547 |
| 4,773,939 | 9/1988 | Meffert | 134/10 |
| 4,978,526 | 12/1990 | Gesslein | 424/70 |

FOREIGN PATENT DOCUMENTS

| | | | |
|---|---|---|---|
| 752813 | 2/1967 | Canada | 252/547 |
| 0299176 | 1/1989 | European Pat. Off. | |
| 1769718 | 7/1971 | Fed. Rep. of Germany | |

OTHER PUBLICATIONS

Gawish, S. M., et al., "Cationic Surface Active Agents", J. Am. Oil Chemist's Soc., vol. 55, pp. 745–747, Oct. 19878.

Primary Examiner—Dennis Albrecht
Attorney, Agent, or Firm—Birch, Stewart, Kolasch & Birch

[57] ABSTRACT

A cationic compound is useful for a cleaning agent such as shampooing and defined by the formula (I):

$$R^1\overset{O}{\underset{\underset{G}{|}}{C}}N-(CH_2)_m\underset{\underset{E}{|}}{N}-(CH_2)_n\underset{\underset{Y}{|}}{C}HCH_2\overset{R^2}{\underset{\underset{R^4}{|}}{N^{\oplus}}}-R^3.A^{\ominus} \quad (I)$$

in which R1 is straight or branched and an alkyl having 7 to 15 carbon atoms or an alkenyl having 7 to 15 carbon atoms; R2, R3 and R4, independently of one another, are an alkyl having 1 to 3 carbon atoms; G is hydrogen atom, an alkyl having 1 to 3 carbon atoms or a hydroxyalkyl having 1 to 3 carbon atoms, E is hydrogen atom, an alkyl having 1 to 3 carbon atoms, a hydroxyalkyl having 1 to 3 carbon atoms or an ammonium group having the formula (II):

$$-(CH_2)_n\underset{\underset{Y}{|}}{C}HCH_2\overset{R^2}{\underset{\underset{R^4}{|}}{N^{\oplus}}}-R^3.A^{\ominus} \quad (II)$$

Y being hydrogen atom or hydroxy, A being hydroxy, a halogen atom or an alkylsulfate having 1 to 4 carbon atoms, m being 2 or 3, n being zero or an integer of 1 to 5, provided that (1) when G is an alkyl or a hydroxyalkyl, E is neither an alkyl nor a hydroxyalkyl, (2) when n is 1, Y is hydrogen atom or hydroxy and when n is zero, 2, 3, 4 or 5, Y is hydrogen atom and (3) G and E cannot both be hydrogen.

13 Claims, No Drawings

MILD CATIONIC SURFACTANTS HAVING GOOD FOAMING CONDITIONING PROPERTIES AND CLEANING COMPOSITIONS

FIELD OF THE INVENTION

The present invention relates to new cationic compounds and processes for producing them. In particular, the present invention relates to new cationic compounds useful as a surfactant for washing the hair or body which has a mild effect on the skin and which exhibits high foaming power and cleansing power as well as processes for producing the same.

The present invention relates to a detergent or cleaning composition which only slightly irritates the skin and hair and which has detergency, foaming and conditioning properties suitable for use as a body shampoo, hair shampoo or the like.

DESCRIPTION OF RELATED

Recently not only surface activity but also excellent properties such as biodegradability, safety and as low as an irritative effect on the eyes and skin as possible are required of surfactants to be used for detergents. Acylated amino acid surfactants and imidazoline surfactants are recently widely used as the surfactants satisfying these requirements.

However, although these surfactants are usually safe their foaming power and detergency power which are particularly important properties of surfactants are insufficient and, therefore, they are not frequently used alone as shampoo ingredient or the like but they are usually used in combination with an anionic surfactant such as an alkyl ether sulfate or alkyl sulfate.

Such an anionic surfactant which strongly irritates the skin might make the skin rough. On the other hand, cationic surfactants have never been used as the detergent, since they usually strongly irritate the skin. No cationic surfactant usable as a detergent base having a high foaming power and safety has been found as yet.

Under these circumstances, development of a cationic surfactant having high foaming power and detergency power and high safety is eagerly demanded. If such a cationic surfactant is developed, it would be useful as a new detergent capable of exhibiting the characteristic cationic properties.

In these days in addition to surface-active properties such as foaming and detergency properties, biodegradability for safety and a low irritative effect to the eyes and the skin are required for a detergent and cleaning agent for use on the human body.

Although anionic surfactants usually used as a main ingredient of detergents [such as soap, linear alkylbenzenesulfonates (LAS), alkylsulfuric ester salts (AS), polyoxyethylene alkyl ether sulfuric esters (AES) and α-olefinsulfonates (AOS)] have excellent detergency and foaming powers, they irritate user's eyes and skin. On the other hand, those proposed as low irritating surfactants such as monoalkylphosphoric esters and N-acylamino acid salts, e.g., N-acylglultamic salts, N-acyl-N-alkyl-β-alanine salts and N-acyl-N-alkylglycine salts do not have sufficient properties required of the detergents, such as hard water resistance, foaming and detergency powers, though they only slightly irritate the skin. Further it is said to be difficult to use a cationic surfactant, such as a mono- or dialkyltrimethylammonium salt, as main ingredient of the detergents from the viewpoints of irritation, detergency and foaming powers. Thus they have not been used as the main ingredient of a detergent composition.

Therefore, it is eagerly demanded to develop a detergent which only slightly irritates the user's hair and skin and which has excellent detergency and foaming powers, foam quality, hard water resistance and conditioning properties.

SUMMARY OF THE INVENTION

After intensive investigations on compounds having excellent detergency power and foaming power and high safety usable as a detergent for the hair and body, the inventors have found that the object of the invention can be attained by new cationic compounds of the general formula (I) given below. The present invention has been completed on the basis of this finding.

The invention provides a cationic compound defined by the formula (I):

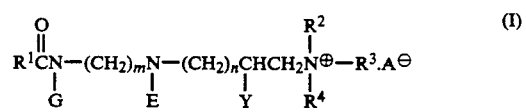

in which R1 is straight or branched alkyl having 7 to 15 carbon atoms or an alkenyl having 7 to 15 carbon atoms; R2, R3 and R4, independently of one another, are an alkyl having 1 to 3 carbon atoms; G is hydrogen atom, an alkyl having 1 to 3 carbon atoms or a hydroxyalkyl having 1 to 3 carbon atoms, E is hydrogen atom, an alkyl having 1 to 3 carbon atoms, a hydroxyalkyl having 1 to 3 carbon atoms or an ammonium group having the formula (II):

Y being hydrogen atom or hydroxy, A being hydroxy, a halogen atom or an alkylsulfate having 1 to 4 carbon atoms, m being 2 or 3, n being zero or an integer of 1 to 5, provided that (1) when G is an alkyl or a hydroxyalkyl, E is neither an alkyl nor a hydroxyalkyl and (2) when n is 1, Y is hydrogen atom or hydroxy and when n is zero, 2, 3, 4 or 5, Y is hydrogen atom.

The invention further provides a process for producing the above shown compound, which comprises the step of reacting a cyclic amine having the formula (2) and/or an amideamine having the formula (3) with a cationizing agent having the formula (4).

Another process for producing the compound, having the formula (I) in which n is 1 and Y is hydroxy, comprises the step of reacting a cyclic amine having the formula (2) and/or an amideamine having the formula (3) with a cationizing agent having the formula (5).

-continued

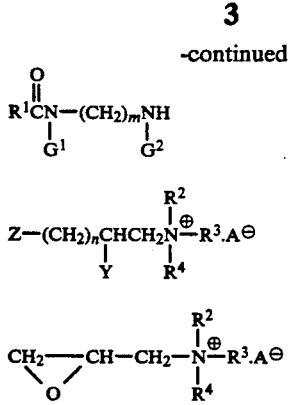

The invention provides a mixture of at least two cationic compounds, that is, a cationic surfactant composition which comprises (a) a cationic compound having the formula (I) which G is hydrogen atom, E is a hydrogen atom, an alkyl having 1 to 3 carbon atoms or hydroxyalkyl having 1 to 3 carbon atoms and (b) another cationic compound having the formula (I) in which G is the same hydrogen atom, an alkyl having 1 to 3 carbon atoms or a hydroxyalkyl having 1 to 3 carbon atoms and E is an ammonium group having the formula (II). Both of G and E are not hydrogen atom at a time.

The composition further comprises a cationic compound having the formula (I) in which G is an alkyl having 1 to 3 carbon atoms or a hydroxyalkyl having 1 to 3 carbon atoms and E is hydrogen atom.

The cationic compound of the invention includes two embodiments: One has the formula (I) in which R1 is straight or branched and an alkyl having 7 to 15 carbon atoms or an alkenyl having 7 to 15 carbon atoms; R2, R3 and R4, independently of one another, are an alkyl having 1 to 3 carbon atoms; G is hydrogen atom; E is an alkyl having 1 to 3 carbon atoms or a hydroxyalkyl having 1 to 3 carbon atoms; Y is hydrogen atom or hydroxy, A is hydroxy, a halogen atom or an alkylsulfate having 1 to 4 carbon atoms; m is 2 or 3; n is zero or an integer of 1 to 5; provided that when n is 1, Y is hydrogen atom or hydroxy and when n is zero, 2, 3, 4 or 5, Y is hydrogen atom.

The other embodiment has the formula (I) in which R1 is straight or branched alkyl having 7 to 15 carbon atoms or an alkenyl having 7 to 15 carbon atoms; R2, R3 and R4, independently of one another, are an alkyl having 1 to 3 carbon atoms; G is an alkyl having 1 to 3 carbon atoms or a hydroxyalkyl having 1 to 3 carbon atoms; E is hydrogen atom or an ammonium group having the formula (II); Y is hydroxy; A is a halogen or an alkylsulfate having 1 to 4 carbon atoms; m is 2 or 3; and n is zero or an integer of 1 to 5, with the same proviso as shown above.

The invention provides a cleaning composition which comprises the cationic compound and a carrier.

Another cleaning composition comprises the cationic compound and another amphoteric or nonionic surfactant.

The cleaning composition further comprises an additive for shampooing.

The cleaning composition further comprises a water-soluble polymer, an anionic polymer, another cationic surfactant or a water-dispersible silicone compound.

The invention provides another cleaning composition which comprises a cationic compound having the formula (I') defined below, having the same general formula as (I), but having different definitions of the substituents in which R1 is straight or branched and an alkyl having 7 to 21 carbon atoms or an alkenyl having 7 to 21 carbon atoms; R2, R3 and R4, independently of one another, are an alkyl having 1 to 4 carbon atoms or a hydroxyalkyl having 1 to 4 carbon atoms; G is hydrogen atom; E is hydroxyethyl; Y is hydroxy; A is a halogen atom or an organic anion; m is 2; and n is 1, and a carrier.

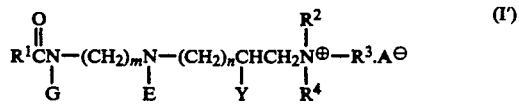

The present invention provides a new cationic compound represented by the general formula (1) and a surfactant prepared therefrom.

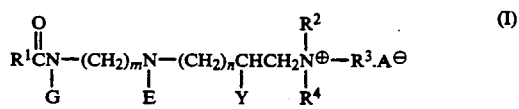

wherein $R^1$ represents a straight chain or branched alkyl or alkenyl group having 7 to 15 carbon atoms, $R^2$, $R^3$ and $R^4$ may be the same or different from one another and each represent an alkyl group having 1 to 3 carbon atoms, G represents H or an alkyl or hydroxyalkyl group having 1 to 3 carbon atoms, E represents H or an alkyl or hydroxyalkyl group having 1 to 3 carbon atoms or a group of the formula:

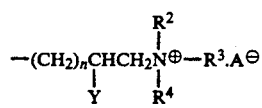

with the proviso that when G represents an alkyl or hydroxyalkyl group having 1 to 3 carbon atoms, E is neither an alkyl nor a hydroxyalkyl group having 1 to 3 carbon atoms, Y represents H or a hydroxyl group, A represents OH, a halogen atom or an alkylsulfuric acid group having 1 to 4 carbon atoms, m represents an integer of 2 or 3 and n represents 0 or an integer of 1 to 5, with the proviso that when n is 1, Y is H or a hydroxyl group, and when n is 0, 2, 3, 4 or 5, Y is H.

A detailed description will now be made of the present invention.

The cationic compounds of the above general formula (I) are not disclosed in the literature or patent gazettes, so that the cationic compounds of the present invention are new compounds.

Examples of the cationic compounds include the following compounds:

[Chemical formula 1]

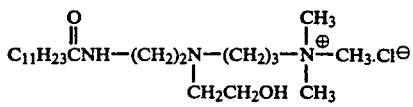

-continued

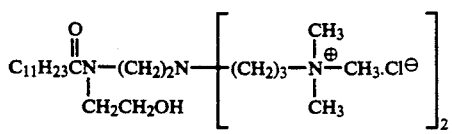

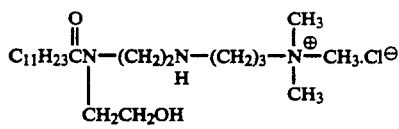

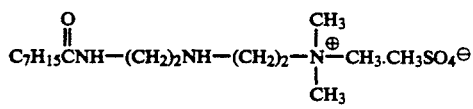

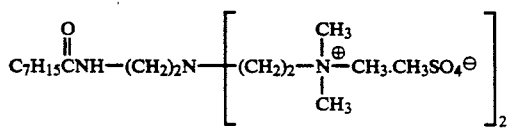

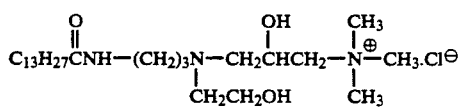

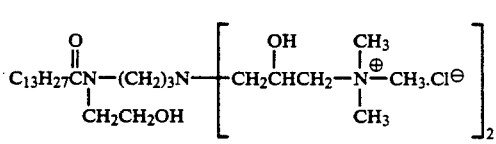

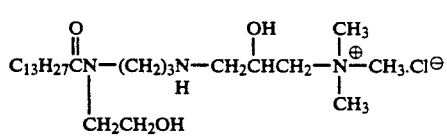

The cationic compounds of the present invention represented by the above general formula (1) can be produced by either of the following two production processes <1> and <2>:

Production process <1>

The cationic compound of the present invention represented by the above general formula (I) is produced by reacting a cyclic amine of the general formula (2)

[Chemical formula 12]

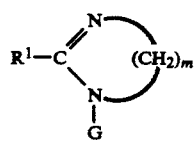 (2)

wherein $R^1$, G and m are as defined above or an amidoamine (hereinafter referred to as "starting amine compounds") of the general formula (3):

[Chemical formula 13]

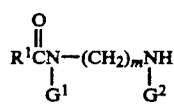 (3)

wherein $R^1$ and m are as defined above and $G^1$ and $G^2$ each represent H or an alkyl or hydroxyalkyl group having 1 to 3 carbon atoms with the proviso that at least one of $G^1$ and $G^2$ represents H, with a cationizing agent of the general formula (4):

[Chemical formula 14]

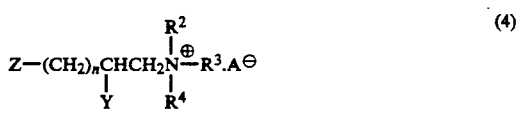 (4)

wherein $R^2$, $R^3$, $R^4$, Y, A and n are as defined above and Z represents a halogen atom,
the cationizing agent (4) being used in an amount of 1 to 3 mol per mol of the starting amine compound. This process can be illustrated by the following reaction scheme:

[Chemical formula 15]

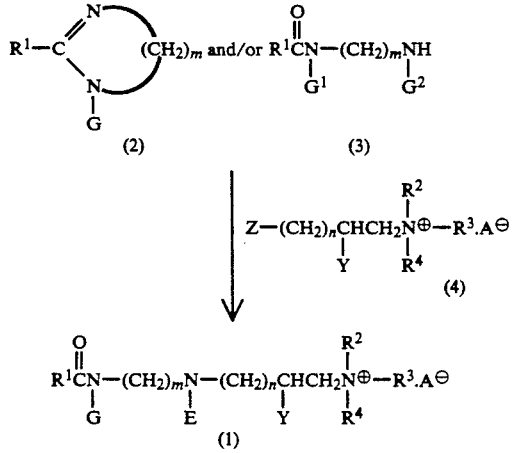

wherein $R^1$, $R^2$, $R^3$, $R^4$, G, $G^1$, $G^2$, E, Y, A, m, n, and Z are as defined above.

In the reaction of the starting amine compound with agent (4), it is preferred to adjust a pH of the reaction mixture at 7 to 12 after the dropwise addition of an aqueous solution of agent (4) to a solution of the starting amine compound in an alcohol. For this purpose, a solution of an alkali such as sodium hydroxide or potassium hydroxide is added to the reaction solution, if necessary. The pH of the reaction system is kept in the above-described range during the reaction in order to react the starting amine with the cationizing agent (4). From the viewpoint of the reaction velocity, the pH is preferably at least 7. When the pH exceeds 12, the cationizing agent (4) is hydrolyzed unfavorably. Although the reaction proceeds even at ambient temperature, the higher the temperature, the higher the reaction velocity. However, the hydrolysis of the cationizing agent (4) is accelerated at a high temperature or high pH. Thus the temperature is not higher than 100° C, preferably not higher than 90° C.

The molar ratio of the cationizing agent (4) to the starting amine compound in this production process is usually preferably 1/1 to 3/1, still preferably 1.1/1 to 1.5/1. When the amount of the cationizing agent (4) is below this range, the conversion is reduced and, on the contrary, when it is above this range, the reaction mixture will unfavorably contain a large amount of the cationizing agent (4) or a hydrolyzate thereof. The termination of the reaction of the starting amine compound with the cationizing agent (4) can be confirmed by analyzing the amount of the remaining starting amine compound during the reaction by high-performance liquid chromatography.

The reaction solution in the process of the present invention may be an aqueous solution, or a solution in a mixture of water with a lower alcohol such as ethanol or isopropyl alcohol or with a diol such as 1,3-propanediol or propylene glycol.

The cyclic amine (2) and amidoamine (3) used as the starting amine compound in the process of the present invention are produced by the following processes:

[Synthesis of cyclic amine (2)]

A fatty acid or its ester of the general formula (6):

[Chemical formula 16]

  (6)

wherein $R^1$ is as defined above and T represents H or an alkyl group having 1 to 3 carbon atoms, is reacted with a diamine of the general formula (7):

$H_2N(CH_2)_m NH—G$  (7)

wherein G and m are as defined above, in a molar ratio of 1/1 to ⅛ to obtain a cyclic amine (2).

This reaction can be shown by the following reaction formula:

[Chemical formula 17]

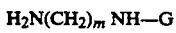

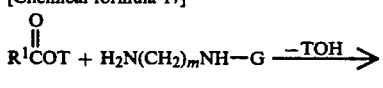

wherein $R^1$, T, G and m are as defined above.

The reaction of the fatty acid or its ester (6) with the diamine (7) is conducted by heating under reduced pressure to synthesize the cyclic amine (2) by dehydration or by removal of a lower alcohol (TOH; T being as defined above).

[Synthesis of amidoamine (3)]

The amidoamine (3) can be produced by hydrolyzing the cyclic amine (2) under an acidic or alkaline condition or by reacting a fatty acid or its ester (6) with a diamine (7) and then hydrolyzing the resulting cyclic amine (2) without isolation thereof.

These reactions can be represented by the following reaction formulae:

[Chemical formula 18]

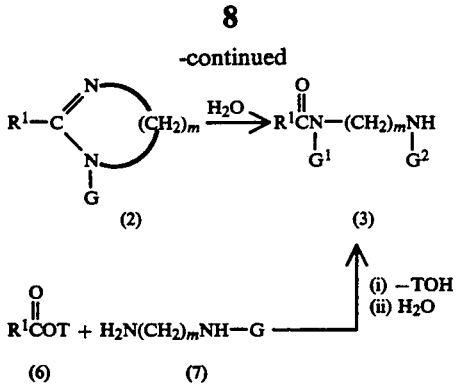

wherein $R^1$, G, $G^1$, $G^2$, T and m are as defined above.

Production process <2>

The cationic compounds of the general formula (1-1) which correspond to the cationic compounds (1) of the present invention wherein n represents 1 and Y represents a hydroxyl group are produced by reacting a starting amine compound [cyclic amine (2) and/or amidoamine (3)] with a cationizing agent of the general formula (5):

[Chemical formula 19]

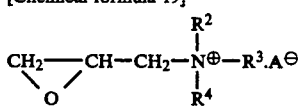

wherein $R^2$, $R^3$, $R^4$ and A are as defined above, in a molar ratio of the cationizing agent (5) to the starting amine compound of 1/1 to 3/1. This production process can be shown by the following reaction scheme:

[Chemical formula 20]

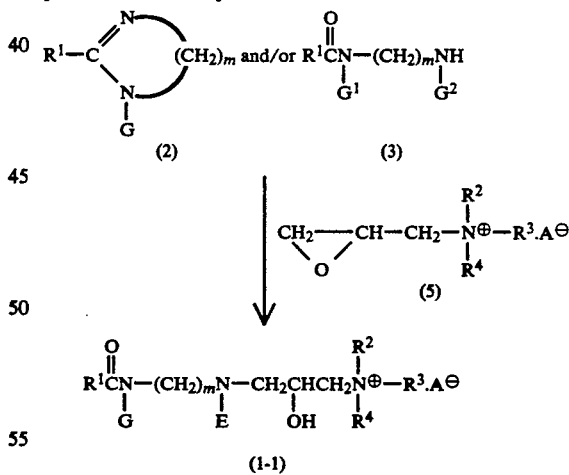

wherein $R^1$, $R^2$, $R^3$, $R^4$, G, $G^1$, $G^2$, E, A and m are as defined above.

The molar ratio of the cationic compound (5) to the starting amine compound in the reaction is 1/1 to 3/1. When the molar ratio is below this range, the reactivity is reduced and, on the contrary, when it is above this range, the reaction mixture unfavorably contain a large amount of a hydrolyzate of the cationizing agent (5). The reaction temperature ranges from 30° to 120° C., preferably from 50° to 90° C. When the reaction temperature is below this range, the reaction velocity is low and, on the contrary, when it is above this range, coloration or the like unfavorably results. To secure the reactivity and to conduct the intended reaction of the starting amine compound with the cationizing agent (5), it is preferred that a suitable amount of an aqueous alkali solution be used for keeping the pH in the range of 7 to 12. When the pH is below this range, the reaction velocity is reduced and, on the contrary, when it is above this range, by-products are formed in a large amount to reduce the yield.

The process for synthesizing the starting amine compound used in the production process <2> is the same as that used in production process <1>.

All of the reactions of the present invention can be conducted in air or in an inert gas atmosphere. The latter is preferred from the viewpoint of preventing coloration or the like.

Examples of the fatty acids or their esters of the above general formula (6) used in the present invention include octylic acid, capric acid, lauric acid, myristic acid, palmitic acid and coconut fatty acids or lower alcohol esters of them. Examples of the diamines of the above general formula (7) include ethylenediamine, N-methylethylenediamine, N-ethylethylenediamine, N-isopropylethylenediamine, aminoethylethanolamine, N-(2-hydroxypropyl)ethylenediamine, N-(3-hydroxypropyl)ethylenediamine, N-methyltrimethylenediamine, N ethyltrimethylenediamine and N-propyltrimethylenediamine.

The above-described cationic compounds having a surface-activity are used as surfactants. A surfactant comprising a mixture of the following cationic compounds (a) and (b) or further comprising the following cationic compound (c) mixed therewith is particularly preferably used:

(a) a cationic compound of the above general formula (1) wherein G represents H and E represents H or an alkyl or hydroxyalkyl group having 1 to 3 carbon atoms, (b) a cationic compound of the above general formula (1) wherein G represents H or an alkyl or hydroxyalkyl group having 1 to 3 carbon atoms and E represents a group of the formula:

[Chemical formula 21]

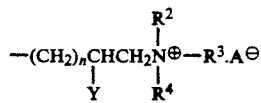

wherein $R^2$, $R^3$, $R^4$, Y, A and n are as defined above. and (c) a cationic compound of the above general formula (1) in which G is an alkyl having 1 to 3 carbon atoms or a hydroxyalkyl having 1 to 3 carbon atoms and E is H.

The invention provides a cleaning or detergent composition comprising as the active component a cationic compound having the formula (I) or (I'). The composition has little irritancy to the skin and the hair of a human user. It is improved in view of foaming power, detergency power and resistance to hard water.

The detergent composition of the present invention comprising the quaternary ammonium salt compound of the above general formula (I) as the main detergent base is suitable for use as a hair shampoo or skin cleaner for infants, shampoo for people who shampoo everyday, shampoo for people who are obliged to come into contact with shampoos for a long period of time as in the hair stylist profession, or suitable for use as light-duty detergents for fibers such as wool, or a light-duty surface detergent for metals and tablewares.

The amount of the quaternary ammonium salt compound of the above general formula (I) in the detergent composition of the present invention is preferably 0.1 to 50% by weight when the detergent is a liquid, 0.1 to 80% by weight when it is a paste or 50 to 99% by weight when it is a solid or powder.

The foaming properties of the detergent composition of the present invention are further improved by using the quaternary ammonium salt compound of the above general formula (I) in combination with an ordinary ampholytic or nonionic surfactant. Examples of the ampholytic surfactants include amidebetaine, carbobetaine, sulfobetanine, phosphobetaine and hydroxysulfobetaine. Examples of the nonionic surfactants include amine oxides, saccharide nonionic surfactants such as alkyl glucosides, and mono- and dialkanolamides.

The detergent composition of the present invention may contain, in addition to the quaternary ammonium salt compounds of the above general formula (I) and the above-described surfactant, polymers such as water soluble polymers, e.g. carboxymethylcellulose; anionic polymers, e.g. acrylic polymers; and water dispersible silicone derivatives as the conditioning component. Further long chain cationic surfactants, higher alcohols, etc., can also be added to the composition. If necessary, flavors, colorants, antiseptics, antioxidants, thickening agents, medicinal components such as dandruff removers, sterilizers, antiinflammatory agents and vitamins, and components described in the Encyclopedia of Shampoo Ingredients (Micelle press, 1985) can be added to the composition.

The above shown explanation about the composition including the cationic compound having the formula (I) applies to the case for the formula (I').

Preferred quaternary ammonium salt compounds of the above general formula (1) are those wherein $R_1$ represents a straight-chain or branched alkyl or alkenyl group having 11 to 17 carbon atoms. Still preferred are those wherein the group $R_1CO-$ represents a lauroyl or myristoyl group and $R_2$, $R_3$ and $R_4$ each represent a methyl group.

The composition may further comprise another cationic surfactant such as a quaternary ammonium salt having the formula (15) or (16) in which at least one of R5, R6, R7 and R8, independently of one another, is an alkyl or an alkenyl, each of which may have a substituent such as an alkoxy, an alkenyloxy, an alkanoylamino and alkenoylamino, having in total 8 to 28 carbon atoms and the balance is benzyl, an alkyl having 1 to 5 carbon atoms or a hydroxyalkyl having 1 to 5 carbon atoms; R9 is an alkylene having 2 or 3 carbon atoms; X is a halogen ion or an organic ion; and n is an integer of 1 to 20.

The quaternary ammonium salt (15) includes preferred embodiments, branched, having the formulae (17), (18) and (19), respectively. In the formulae, R10 is a mixture of (a) and (b), each below defined, a ratio of (a) to the sum total of (a) and (b) ranging between 10 and 100 percent. (a) a branched alkyl having the formula: CH3'(CH2)p—CH(R16)CH2—, R16 is methyl or ethyl, p is such an integer as to make the total carbon number of 8 to 16 in the alkyl; (b) a straight alkyl having the formula: CH3—(CH2)q—, q is an integer of 7 to 15. R11 and R12 is benzyl, an alkyl having 1 to 3 carbon atoms or a hydroxyalkyl having 1 to 3 carbon atoms, R13 and R14 is an alkyl having 2 to 12 carbon atoms, R15 is R13—CH2—CH2—CH(R14)CH2—or an alkyl having 1 to 3 carbon atoms, R17 is CH3—(CH2-)s—CH(CH3)—(CH2)t— or an alkyl having 1 to 3 carbon atoms, s is an integer of 2 to 14, t is an integer of 3 to 11, the sum total of s and t makes 9 to 12, X is a halogen ion or an organic ion.

The branched quaternary ammonium salt (17) is obtained from an oxoalcohol having 8 to 16 carbon atoms, preferably including a dialkyldimethylammonium salt, a dialkylmethylhydoxyethylammonium salt and a dialkylmethylbenzylammonium salt, the alkyl being derived from the oxoalcohol.

The R10 of the formula (17) is preferred to have a branched extent of 10 to 50 percent and the following carbon number distribution is preferable: C8 to C11 of 5% or below, C12 of 10 to 35%, C13 of 15 to 40%, C14 of 20 to 45%, C15 of 5 to 30% and C16 of 5% or below.

A dialkyldimethylammonium chloride in which the alkyl has 8 to 16 carbon atoms and a branched extent of 10 to 50% is more preferable.

The ammonium salt (18) is obtained from a Gerber alcohol having 8 to 28 carbon atoms, preferably including an alkyltrimethylammonium salt such as 2-decyltetradecyltrimeathylammonium chloride and 2-dodecylhexadecyltrimethylammonium chloride, an alkyldimethylbenzylammonium salt, a dialkyldimethylammonium salt such a di-2-hexyldecyldimethylammonium chloride and di-2-octyldodecyldimethylammonium chloride, a dialkylmethylhydroxyethylammonium salt and a dialkylmethylbenzylammonium salt, each alkyl being derived from the Gerber alcohol.

The methyl-quaternary ammonium chloride (19) is preferred to have a sum total of s and t of 15.

The counter ion for X includes a halogen ion such as chlorine, iodine and bromine and an organic anion such as methosulfate, ethosulfate, methophosphate and ethophosphate.

The cleaning composition of the invention may further comprise a water-soluble, anion group having polymer. This polymer includes cellulose derivatives such as carboxymethylcellulose, chitin derivatives such as carboxymethylchitin, xanthane gum and carrageeman, acacia and polymers or copolymers of an alginic acid derivative, acrylic acid derivative or N-methacroylethyl-N,N-dimethylammonium-N-methylcarboxybetain.

The cleaning composition of the invention may further comprise a silicone derivative such as (21) dimethylpolysiloxane in which n is 3 to 20,000, (22) methylphenylpolysiloxane in which n' is 1 to 20,000 and the sum total of a and b is 1 to 500, (23) a polyether-modified silicone in which R' is —(CH2)3—O—(C2H4O)x-1—(C3H6O)y1—A, A is an alkyl having 1 to 12 carbon atoms or hydrogen, xl is 0 to 50, yl is 0 to 50, the sum total of xl and yl is 1 or larger, ml is 1 to 2000 and nl is 1 to 1000, (24) an epoxy-modified silicone in which x2 is 1 to 500, preferably 1 to 250, y2 is 1 to 50, preferably 1 to 30 and R5 is an alkylene having 1 to 3 carbon atoms, (25) a fluorine-modified silicone in which x3 is 1 to 400, preferably 1 to 250, (26) an alcohol-modified silicone in which x4 and y4 are 1 to 500, preferably 1 to 200, R6 is Cn"H2n" and n" is zero to 4, (27) an alkyl-modified silicone in which x5 and y5 are 1 to 500, preferably 1 to 200, R7 is an alkyl having 2 to 18 carbon atoms, R8 is Cn"H2n, n" is zero to 4 and R9 is an alkyl having 10 to 16 carbon atoms, (28) an alkoxy-modified silicone in which R10 is methyl or phenyl, R11 is an alkyl having 1 to 28 carbon atoms, preferably 12 to 22, and k is zero or an integer of 1 to 6 and (29) an amino-modified silicone in which R12 is methyl or hydroxy, R13 is methyl or hydrogen, R14 is —R16—(R17)d—(NHCH2CH2)e—NR18R19 or —R16—(R17)d-(NHCH2CH2)e-N+(R18)3.Z-, R16 is a divalent hydrocarbon group, R17 is —OCH2CH2—, —OCH(CH3)CH2—, —OCH2CH(OH)CH2—or —OCH2CH(CH2OH)—, R18 and R19 are hydrogen or a monovalent hydrocarbon group, d and e is zero or an integer of 1 to 6, Z- is a halogen ion or an organic ion, R15 is hydroxy, a hydroxyalkyl, an oxyalkylene or a polyoxyalkylene, 12, m3 and n3 are an integer depending on the molecular weight, having the respective formulae. The amino-modified silicone includes embodiments having the formulae (30) and (31).

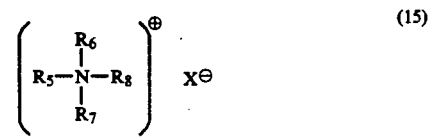

(15)

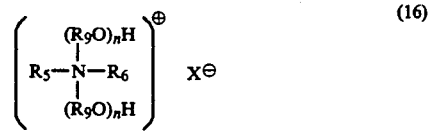

(16)

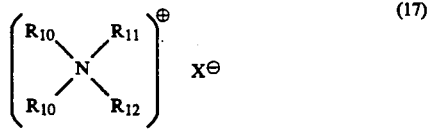

(17)

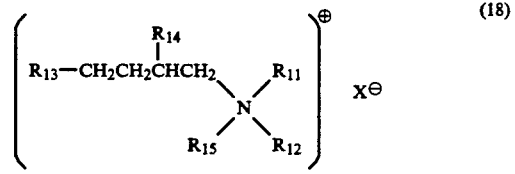

(18)

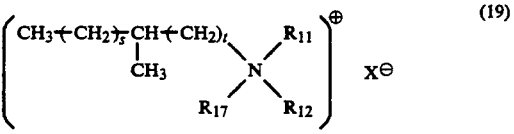

(19)

$(CH_3)_3SiO[(CH_3)_2SiO]_nSi(CH_3)_3$ (21)

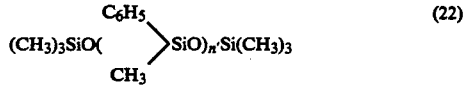

(22)

$(CH_3)_3SiO[(CH_3)_2SiO]_a[(C_6H_5)_2SiO]_bSi(CH_3)_3$ (23)

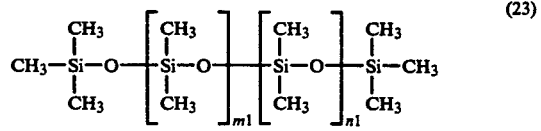

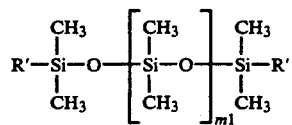

-continued

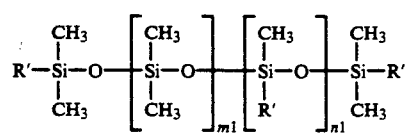

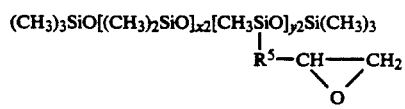 (24)

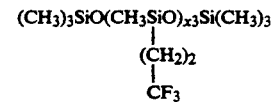 (25)

 (26)

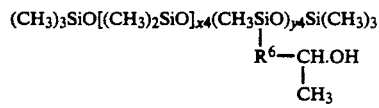 (27)

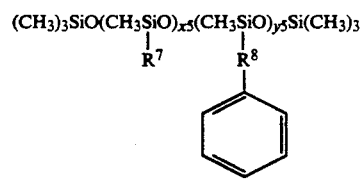 (27)

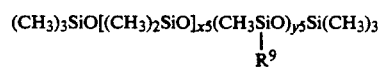 (28)

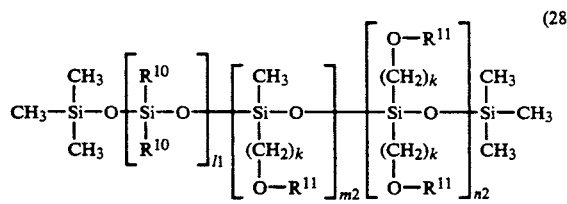 (28)

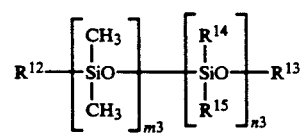 (29)

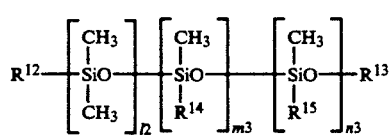 (30)

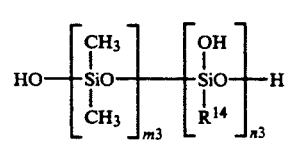

-continued

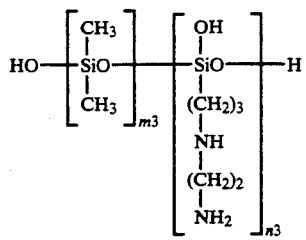 (31)

The following Examples will further illustrate the present invention, which by no means limit the invention.

EXAMPLE 1

268 g (1 mol) of 1-hydroxyethyl-2-undecylimidazoline synthesized by an ordinary method, 54 g of water and 1.2 g of sodium hydroxide were placed in a 1-l four-necked flask provided with a stirrer, condensing tube, dropping funnel and thermometer and heated to 80° C. under stirring. The stirring was continued at that temperature for about 2 h to open the imidazoline ring to thereby obtain N-lauroyl-N'- (2-hydroxyethyl)ethylenediamine. Then 200 g of ethanol was added thereto and the temperature was elevated to 80° C. under stirring. pH electrodes were introduced into the liquid in order to determine the pH of the reaction mixture. A 40% aqueous NaOH solution was added dropwise thereto to adjust the pH to 10. Thereafter 489 g (1.3 mol) of a 50% aqueous solution of 3 chloro-2-hydroxypropyl-N,N,N-trimethylammonium chloride (MW: 188) was added dropwise for 2 h while a 40% aqueous NaOH solution was suitably added dropwise thereto to keep the pH at 10. After the completion of the addition of 3-chloro-2-hydroxypropyl-N,N,N-trimethylammonium chloride, stirring was continued at that temperature while the pH was kept at 10 and the amount of remaining N-lauroyl-N'-(2-hydroxyethyl)ethylenediamine was determined by high-performance liquid chromatography at intervals of 1 h.

Six hours after the completion of the addition of 3-chloro -2-hydroxypropyl-N,N,N-trimethylammonium chloride, it was confirmed that the concentration of N-lauroyl-N'-(2-hydroxyethyl)ethylenediamine in the reaction system reached 1% or less and the reaction was completed.

The reaction liquid was purified by electrodialysis, partially evaporated to dryness and dissolved in ethanol. The resultant solution was analyzed by high-performance liquid chromatography to find that the following three components were obtained as the main components:

[Chemical formula 22]

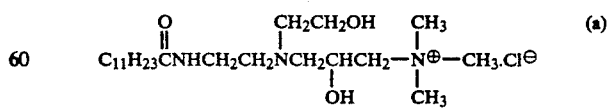 (a)

(98% by weight based on the solid obtained by evaporation)

Results of IR analysis and mass spectrometric analysis

<IR analysis>

A strong absorption peculiar to amides was observed at 1650 cm$^{-1}$ (6.06 μ).

<Mass spectrometric analysis>

(Mass spectrometric analysis described hereinafter was conducted under the following conditions)
Apparatus: SX-102 for mass spectrometric analysis mfd. by JEOL, Ltd.
Determination conditions: introduction method: direct ionization method: FAB (fast atom bombardment)
Analytical results: fragment ion molecular weight 402, 226

Two main peaks were observed, 402 being an (M+-Cl) ion peak, substantiating that the product was the cationic compound of the above-described structure.

[Chemical formula 23]

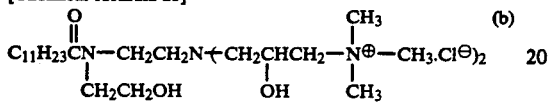

(1% by weight based on the solid obtained by evaporation)

Results of IR analysis and mass spectrometric analysis

<IR analysis>

A strong absorption peculiar to amides was observed at 1650 cm$^{-1}$ (6.06 μ).

<Mass spectrometric analysis>

Analytical results: fragment ion molecular weight 458, 270

[Chemical formula 24]

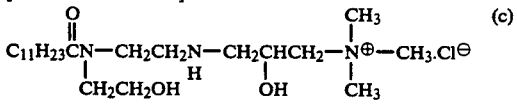

(1% by weight based on the solid obtained by evaporation)

Results of IR analysis and mass spectrometric analysis

<Ir analysis>

A strong absorption peculiar to amides was observed at 1650 cm$^{-1}$ (6.06 μ).

<Mass spectrometric analysis>

Analytical results: fragment ion molecular weight 402, 270

EXAMPLE 2

The same procedure as that of Example 1 was repeated except that 1-hydroxyethyl-2-undecylimidazoline was replaced by 1-hydroxyethyl-2-tridecylimidazoline synthesized by using myristic acid as the starting fatty acid. It was confirmed in the same manner as that of Example 1 that three compounds of the following structures were obtained as the main components.

[Chemical formula 25]

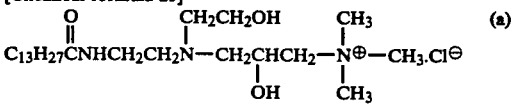

(98% by weight based on the solid obtained by evaporation)

<Mass spectrometric analysis>

Analytical results: fragment ion molecular weight 430, 254

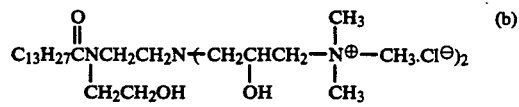

(1% by weight based on the solid obtained by evaporation)

<Mass spectrometric analysis>

Analytical results: fragment ion molecular weight 486, 298

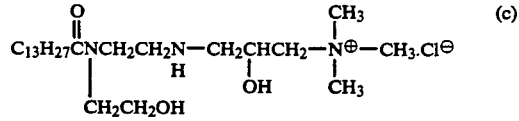

(1% by weight based on the solid obtained by evaporation)

<Mass spectrometric analysis>

Analytical results: fragment ion molecular weight 430, 298

EXAMPLE 3

The same procedure as that of Example 1 was repeated except that 1-hydroxyethyl-2-undecylimidazoline was replaced by 1-hydroxyethyl-2-pentadecylimidazoline synthesized by using palmitic acid as the starting fatty acid. It was confirmed in the same manner as that of Example 1 that three compounds of the following structures were obtained as the main components.

[Chemical formula 26]

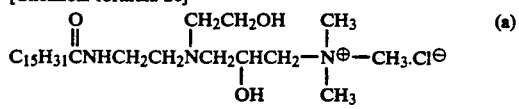

(98% by weight based on the solid obtained by evaporation)

<Mass spectrometric analysis>

Analytical results: fragment ion molecular weight 458, 282

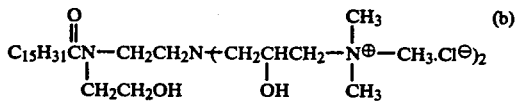

(1% by weight based on the solid obtained by evaporation)

<Mass spectrometric analysis>

Analytical results: fragment ion molecular weight 514, 326

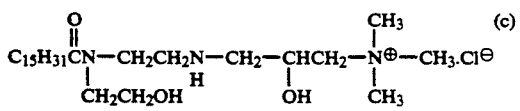

(1% by weight based on the solid obtained by evaporation)

<Mass spectrometric analysis>

Analytical results: fragment ion molecular weight 458, 326

EXAMPLE 4

The same procedure as that of Example 1 was repeated except that N-(3-lauroylaminopropyl)-propylamine synthesized from N-propyl-1,3-trimethylenediamine as the starting diamine and 3-chloropropyl-N,N,N-trimethylammonium chloride as the cationizing agent were used. It was confirmed in the same manner as that of Example 1 that three compounds of the following structures were obtained as the main components.

[Chemical formula 27]

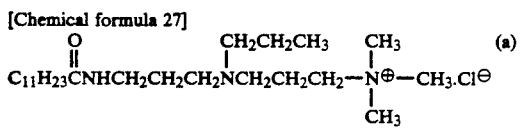

(98% by weight based on the solid obtained by evaporation)

Results of IR analysis and mass spectrometric analysis:

<IR analysis>

A strong absorption peculiar to amides was observed at 1650 cm$^{-1}$ (6.06 μ).

<Mass spectrometric analysis>

Mass spectrometric analysis was conducted under the same conditions as those of Example 1.

Analytical results: fragment ion molecular weight 398, 240

Two main peaks were observed, 398 being an (M+-Cl) ion peak, substantiating that the product was the cationic compound of the above-described structure.

[Chemical formula 28]

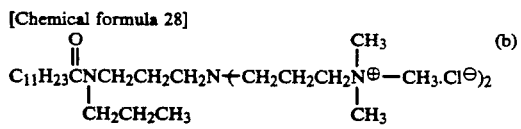

(1% by weight based on the solid obtained by evaporation)

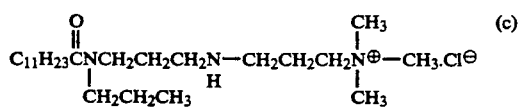

(1% by weight based on the solid obtained by evaporation)

EXAMPLE 5

The same procedure as that of Example 1 was repeated except that 3-chloro-2-hydroxypropyl-N,N,N-trimethylammonium chloride used as the cationizing agent was replaced by 2,3-oxypropyl-N,N,N-trimethylammonium chloride. It was confirmed in the same manner as that of Example 1 that the obtained compounds were the same as the three components given in Example 1.

EXAMPLE 6

752 g (2 mol) of a 50% aqueous solution of 3-chloro-2-hydroxypropyl-N,N,N-trimethylammonium chloride and 800 g of water were placed in a 2-l four-necked flask provided with a stirrer, condensing tube, dropping funnel and thermometer. The temperature was elevated to 70° C. 268 g (1 mol) of 1-hydroxyethyl-2-undecylimidazoline synthesized by an ordinary process was added dropwise thereto for about 2 h while the temperature was kept at that point. pH electrodes were introduced into the liquid mixture in order to determine the pH of the reaction mixture. A 40% aqueous NaOH solution was added dropwise thereto to adjust the pH to 10. Aging was conducted at that temperature for about 6 h while a 40% NaOH was suitably added dropwise thereto to keep the pH at 10. The amount of remaining N-lauroyl-N-(2-hydroxyethyl)-ethylenediamine was determined by high-performance liquid chromatography at intervals of 1 h. It was confirmed that the concentration of N-lauroyl-N-(2-hydroxyethyl)ethylenediamine in the reaction system reached 1% or less and the reaction was completed.

The reaction liquid was purified by electrodialysis, partially evaporated to dryness and dissolved in ethanol. The resultant solution was analyzed by high-performance liquid chromatography to find that the following three components were obtained as the main components:

[Chemical formula 29]

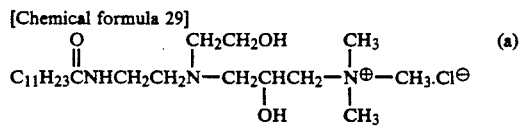

(5% by weight based on the solid obtained by evaporation)

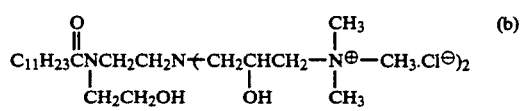

(90% by weight based on the solid obtained by evaporation)

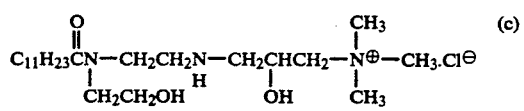

(5% by weight based on the solid obtained by evaporation)

EXAMPLE 7

376 g (1 mol) of a 50% aqueous solution of 3-chloro-2-hydroxypropyl-N,N,N-trimethylammonium chloride and 800 g of water were placed in a 2-l four-necked flask provided with a stirrer, condensing tube, dropping funnel and thermometer. The temperature was elevated to 70° C. 268 g (1 mol) of 1-hydroxyethyl-2-undecylimidazoline synthesized by an ordinary process was added dropwise thereto for about 2 h while the temperature was kept at that point. pH electrodes were introduced into the liquid in order to determine the pH of the reaction mixture. A 40% aqueous NaOH solution was added dropwise thereto to adjust the pH to 10. Aging was conduced at that temperature for about 6 h while at 40% NaOH was suitably added dropwise thereto to the keep pH at 10. The amount of remaining N-lauroyl-N-(2-hydroxyethyl)-ethylenediamine was determined by high-performance liquid chromatography at intervals of 1 h. It was confirmed that the concentration of N-lauroyl-N-(2-hydroxyethyl)ethylenediamine in the reaction system reached 1% or less and the reaction was completed. The reaction liquid was purified by electrodialysis and partially evaporated to dryness. It was found by IR analysis and mass spectrometric analysis that a mixture of the following three components was obtained and that the main component was N-lauroyl-N-(2-hydroxyethyl)-N'-[3-(N'', N'', N''-trimethylammonio)- 2-hydroxyproply]-ethylenediamine chloride of the following structure (c):

[Chemical formula 30]

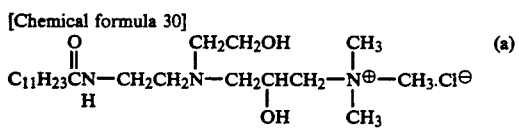

(5% by weight based o the solid obtained by evaporation)

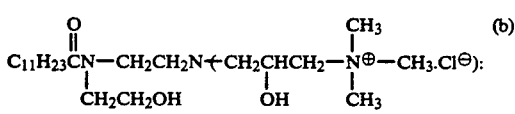

(35% by weight based on the solid obtained by evaporation)

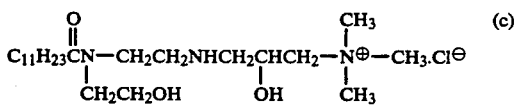

(60% by weight based on the solid obtained by evaporation)

TEST EXAMPLE

The skin-irritating property, foaming power and deterging power of the surfactants produced in Examples 1 through 4, 6 and 7, the following control compounds 1 and 2 known to have a quite mild effect on the skin and control compound 3 having a high foaming power were evaluated by the methods described below. The results are given in Table 1.

<Control compound 1>
Softazolin CH mfd. by Kawaken Fine Chemicals Co., Ltd. (N-cocoyl-N'-hydroxyethyl-N'-(sodium carboxymethyl)ethylenediamine)

<Control compound 2>
Alanon ALE mfd. by Kawaken Fine Chemicals Co., Ltd. (sodium N-lauroyl-N-methyl-$\beta$-alaninate)

<Control compound 3>
Emal TD mfd. by Kao Corporation (sodium lauryl sulfate)

<Evaluation method>
Skin-irritation test:
A 24-hour closed patch test was conducted by using human subjects. In the test, an adhesive plaster for the patch test impregnated with 0.1 ml of a 0.2% aqueous solution of a surfactant as the active ingredient was applied to 20 subjects and kept for 24 h. 24 h after the removal of the adhesive plaster, the irritation was examined. When a clear erythema was observed. The results were judged to be positive. The results of the evaluation were shown in terms of the positive rate.

Foaming power test:
The active ingredient of the surfactant was diluted with 4° DH hard water to a final concentration of 0.2% and the foaming power was determined by the reverse stirring method. The foaming power test was conducted in the presence of 0.3% lanolin at 40° C. and the results were given in terms of the quantity (ml) of the foams.

Detergency power test:
A dirt having substantially the same composition as that of scalp sebum containing 2% of carbon black (i.e. composition comprising 12% of paraffin, 21% of wax ester, 26% of triglyceride, 32% of higher fatty acids, 5% of cholesterol and 2% of monoglyceride) was uniformly applied to a wool muslin cloth having a size of 5 cm×5 cm and dried. The dirty cloth was placed in an about 1,000 ml stainless steel cylinder containing 500 ml of a detergent solution containing 0.6% of the active ingredient of the surfactant and having a pH of 7.0 and hardness of 4° DH. The cylinder shaken in a thermostatic bath at 40° C. for 6 min. Then the cloth was thoroughly rinsed in running water and dried and the reflectivity of the cloth was determined. The deterging rate was determined by the following formula:

$$\text{detergency rate (\%)} = \frac{\text{(Reflectivity after washing)} - \text{(Reflectivity before washing)}}{\text{(Reflectivity of original cloth)} - \text{(Reflectivity before washing)}} \times 100$$

[TABLE 1]

| Performance | Example | | | | | | | Control Compound | | |
|---|---|---|---|---|---|---|---|---|---|---|
|  | 1 | 2 | 3 | 4 | 5 | 6 | 7 | 1 | 2 | 3 |
| Skin irritation (positive rate %) | 0 | 0 | 5 | 10 | 0 | 0 | 0 | 15 | 10 | 90 |
| Foaming power (ml) | 125 | 165 | 150 | 120 | 125 | 130 | 130 | 110 | 85 | 175 |
| Deterging rate (%) | 40 | 45 | 40 | 40 | 40 | 40 | 40 | 45 | 20 | 20 |

EXAMPLE 8

Formation of imidazoline compound 200 g (MW: 200, 1 mol) of lauric acid and 135.2 g (MW: 104, 1.3 mol) of aminoethylethanolamine (AFEA) were placed in a 1-l four-necked flask provided with a stirrer. reflux condenser. thermometer and pressure gauge. The mixture was stirred and heated to 140° C. while 80° C. water was introduced into the reflux condenser. Then the reaction pressure was set at 400 mmHg in 1 h and the reaction was conducted for 2 h to effect amidation. Thereafter the reaction temperature and pressure were changed to 200° C. and 200 mmMg, respectively. In 1.5 h and aging was conducted under these conditions for 1 h. Then the pressure was reduced to 10 mmhg in about 2 h and the reaction was conducted under these conditions for 2 h to remove excess AEEA while vapors of water and excess AEEA formed in this step were collected with a trap cooled with dry ice/methanol.

Thus 268 g of the reaction product mainly comprising 1-hydroxyethyl-2-undecylimidazoline was obtained.

Quaternization

Then 268 g (1 mol) of 1-hydroxyethyl-2-undecylimidazoline produced as described above and 18 g of a 2% aqueous sodium hydroxide solution were placed in a 1-l four-necked flask provided with a stirrer reflux condenser, thermometer and dropping funnel. The temperature was elevated to 80° C. under stirring and the flask was kept at this temperature for 2 h. Then 250 g of ethanol and 250 g of water were added to the flask at the same time. When the temperature was elevated to 80° C. again. 376 g of a 50% aqueous solution of 3-chloro-2-hydroxypropyltrimethyl-ammonium chloride (MW: 188, 1 mol) was added dropwise thereto in 1 h. Then 100 g of a 40% aqueous sodium hydroxide solution was added dropwise thereto in 3 h and aging was conducted for 8 h. Thus a 35% aqueous solution of 2-hydroxy-3-[(2-hydroxyethyl) [2-[(1-oxododecyl)amino]ethyl]amino] propyl-N,N,N-trimethylammonium chloride of the following formula was obtained:

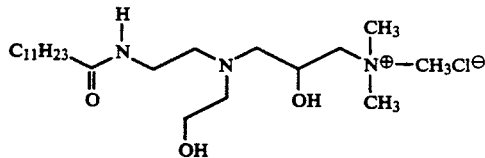

EXAMPLE 9

Formation of imidazoline compound

1-Hydroxyethyl-2-tridecylimldazoline was obtained in the same manner as that of Example 8 except that myristic acid was used as the starting fatty acid.

Quaternization

The reaction was conducted under the same conditions as those of Referential Example 1 except that the above-described 1-hydroxyethyl-2-tridecylimidazoline was used as the starting imidazoilne to obtain a 35% aqueous solution of 2-hydroxy-3-[(2-hydroxyethyl) [2-[(1-oxotetradecyl)-amino]ethyl]amlno]propyl-N,N,N-trimethylammoniumchloride of the following formula:

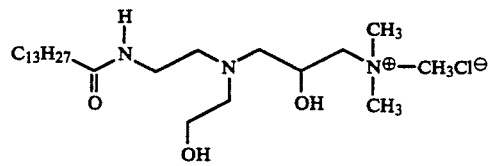

EXAMPLE 10

Formation of imidazoline compound

1-Hydroxyethyl-2-cocoylimidazoline was obtained in the same manner as that of Example 8 except that coconut fatty acids were used as the starting fatty acid.

Quaternization

The reaction was conducted under the same conditions as those of Example 8 except that the above-described 1-hydroxyethyl-2-cocoylmidazoline was used as the starting imidazoline to obtain a 35% aqueous solution of a compound of the following formula:

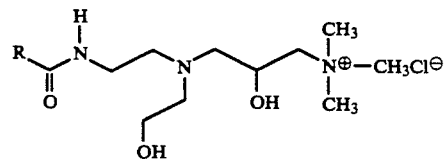

wherein RCO—represents a coconut fatty acid residue.

EXAMPLE 11

Formation of imidazoline compound

An imidazoline compound was formed under the same reaction conditions as those of Example 8 to obtain 1-hydroxyethyl-2-undecylimidazoline.

Quaternization

Then 268 g (1 mol ) of 1-hydroxyethyl-2-undecylimidazoline produced as described above and 18 g of a 2% aqueous sodium hydroxide solution were placed in a 2-l four-necked flask provided with a stirrer, condenser, thermometer and dropping funnel. The temperature was elevated to 80° C. under stirring and the flask was kept at that temperature for 2 h. Then 250 g of ethanol and 250 g of water were added thereto at the same time. When the temperature was elevated to 80° C. again. 436 g of a 50% aqueous solution of N-(3-chloro-2-hydroxypropyl)-N-hydroxyethyl-N, N-dimethylammpnium chloride (MW: 218) prepared from 92.5 g of epichlorohydrin (MW: 92.5 g, 1 mol), 104 g of 35% hydrochloric acid (MW: 36.5, 1 mol) 89 g of dimethylethanolamine (MW: 89, 1 mol) and 150 g of ion-exchanged water was added dropwise thereto in 1 h. Then 100 g of a 40% aqueous sodium hydroxide solution was added dropwise thereto in 3 h and the product was aged for 8 h.

Thus a 35aqueous solution of 2-hydroxy-3-[(2-hydroxyethyl) [2-[(1-oxododecyl)amino] ethyl]-amino]-propyl-N-hydroxyethyl-N,N-dimethylammonium chloride of the following formula was obtained:

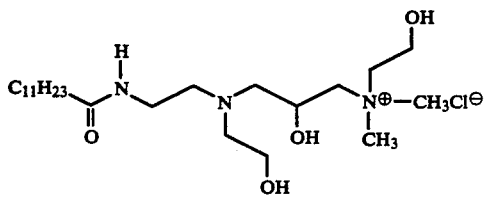

EXAMPLE 12

The foaming properties, skin irritation, deterging power and hard water resistance of the following quaternary ammonium salt cationic surfactants and comparative ones were examined by the test methods described below.

The results are given in Table 2.

<Surfactants used>

Surfactant 1 of the present invention:

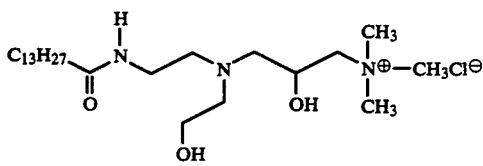

Surfactant 2 of the present invention:

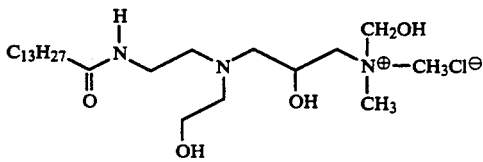

Comparative surfactant 1:

Sodium N-lauroyl-N-methyl-β-alaninate

Comparative surfactant 2:

Triethanolamine lauryl sulfate
Comparative surfactant 3
Cetyitrimethyiammonium chloride <Test method>

Foaming test method, Skin irritation test method and deterging power test were conducted in the same way as the Evaluation method.

The quality of the foam was evaluated according to the following criteria:

o : creamy

: a little rough, and x: rough.

Hard water resistance test:

Calcium chloride was added to a 0.1% aqueous surfactant solution to adjust the hardness to 100° DH. The appearance of the aqueous solution as observed with the naked eye at room temperature.

o: transparent solution obtained.

x: precipitation or floccuration caused.

Conditioning property test:

1 g of a 20% aqueous solution of the active ingredient of the surfactant was applied to 20 g of a bundle of hairs (15 cm) of a Japanese female subject. After foaming followed by rinsing with 40° C. running water and drying with a dryer, the conditioning properties were evaluated by 5 professional panel members.

o: excellent conditioning properties

Δ: sightly insufficient conditioning properties x: poor conditioning properties.

TABLE 2

| | Present invention | | Comparative | | |
|---|---|---|---|---|---|
| | 1 | 2 | 1 | 2 | 3 |
| Skin stimulation | 5 | 5 | 10 | 90 | 90 |
| Quantity of foam (ml) | 165 | 165 | 85 | 165 | 40 |
| Quality of foam | o | o | Δ | x | o |
| Deterging rate (%) | 40 | 30 | 20 | 19 | 10 |
| Hard water resistance | o | o | x | x | o |
| Conditioning properties | o | o | x | x | o |

EXAMPLE 13

A shampoo having the following composition as produced.

The resultant shampoo had high deterging and foaming powers and excellent hard water resistance and only an extremely slight irritation. As for the touch, the hair did not squeak during shampooing and rinsing favorably.

<Composition>

$$C_{13}H_{27}-\underset{O}{\overset{\overset{H}{|}}{C}}-N-CH_2CH_2-N(CH_2CH_2OH)-CH_2CH(OH)CH_2-N^{\oplus}(CH_3)_2-CH_3\ Cl^{\ominus}$$

15% by weight

| | |
|---|---|
| lauryldimethylamine oxide | 3 |
| cetyltrimethylammonium chloride | 2 |
| carboxymethylcellulose*1 | 0.5 |
| hydroxyethylcellulose*2 | 0.1 |
| sodium benzoate | 0.3 |
| colorant | a suitable amount |
| flavor | a suitable amount |
| citric acid | a suitable amount |
| water | q.s. ad 100% by weight |
| pH | 6.5 |

Notes)
*1No 1310 mfd. by Daicel, Ltd.
*2SE-850K mfd. by Daicel, Ltd.

EXAMPLE 14

A body shampoo having the following composition was prepared.

The resultant body shampoo had high deterging power and foaming powers and only an extremely slight irritation. After washing the body with the shampoo, the user felt moist and comfortable.

<Composition>

$$C_{13}H_{27}-\underset{O}{\overset{\overset{H}{|}}{C}}-N-CH_2CH_2-N(CH_2CH_2OH)-CH_2CH(OH)CH_2-N^{\oplus}(CH_3)_2-CH_3\ Cl^{\ominus}$$

15% by weight

| | |
|---|---|
| lauryldimethylamine oxide | 3 |
| polyoxyethylene (3) lauryl glucoside | 5 |

-continued

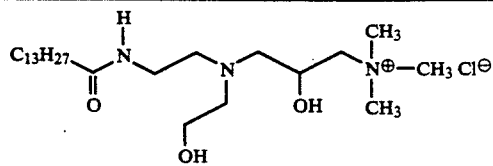

|  | 15% by weight |
|---|---|
| glycerol | 5 |
| sucrose fatty acid ester | 1 |
| methylparaben | 0.3 |
| colorant | a suitable amount |
| flavor | a suitable amount |
| citric acid | a suitable amount |
| water | q.s. ad 100% by weight |
| pH | 7.5 |

We claim:

1. A process for producing a cationic compound having the formula (I):

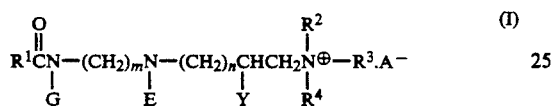

in which $R^1$ is a straight or branched alkyl having 7 to 15 carbon atoms or a straight or branched alkenyl having 7 to 15 carbon atoms; $R^2$, $R^3$ and $R^4$, independently are each an alkyl having 1 to 3 carbon atoms; G is hydrogen, an alkyl having 1 to 3 carbon atoms or a hydroxyalkyl having 1 to 3 carbon atoms, E is hydrogen, an alkyl having 1 to 3 carbon atoms, a hydroxyalkyl having 1 to 3 carbon atoms or an ammonium group having the formula (II):

wherein Y is hydrogen or hydroxy, A is hydroxy, a halogen atom or an alkylsulfate having 1 to 4 carbon atoms, m is 2 or 3, n is zero or an integer of 1 to 5, provided that (1) when G is an alkyl or a hydroxyalkyl, E is neither an alkyl nor a hydroxyalkyl, (2) when n is 1, Y is hydrogen or hydroxy, and when n is zero, 2, 3, 4 or 5, Y is hydrogen atom and (3) G and E cannot be H at the same time which comprises the step of reacting a cyclic amine having the formula (2) and/or an amideamie having the formula (3) with a cationizing agent having the formula (4) or (5)

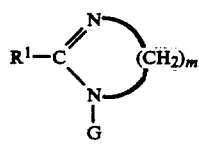

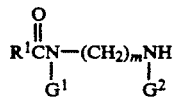

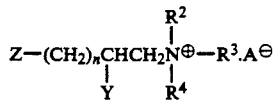

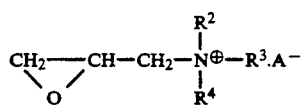

wherein $R^1$, $R^2$, $R^3$, $R^4$, Y, A, m and n are defined in claim 1, Z is a hydrogen atom, and G, $G^1$ and $G^2$ each represent H or an alkyl having 1 to 3 carbon atoms, or hydroxyalkyl groups having 1 to 3 atoms with the proviso that $G^1$ and $G^2$ cannot be H at the same time.

2. A compound which has the formula:

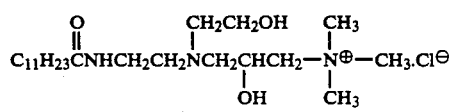

3. A compound which has the formula:

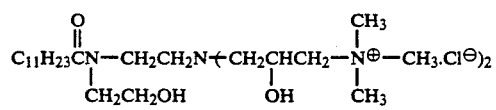

4. A compound which has the formula:

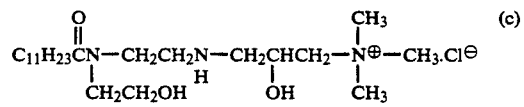

5. A compound which has the formula:

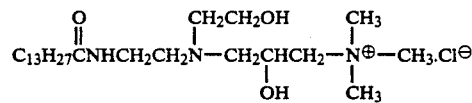

6. A compound which has the formula:

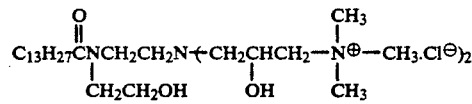

7. A compound which has the formula:

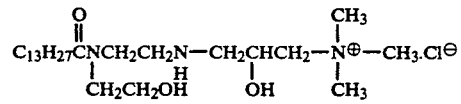

8. A compound which has the formula:

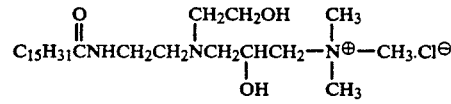

9. A compound which has the formula:

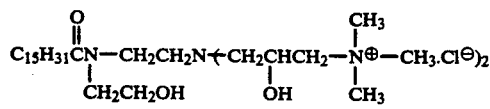

10. A compound which has the formula:

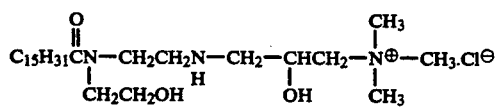

11. A liquid cleaning composition which comprise 0.1 to 50% by weight of the total weight of said liquid cleaning composition of a cationic compound according to any one of claims 2, 3, 4, 5, 6, 7, 8, 9 or 10.

12. A paste cleaning composition which comprise 0.1 to 80% by weight based on the total weight of said paste cleaning composition of a cationic compound according to any one of claims 2, 3, 4, 5, 6, 7, 8, 9, or 10.

13. A solid or powder cleaning composition which comprises 50 to 99% by weight based on the total weight of said solid or powder cleaning composition, a cationic compound according to any one of claims 2, 3, 4, 5, 6, 7, 8, 9 or 10.

* * * * *